United States Patent [19]

Morrison

[11] 4,015,470
[45] Apr. 5, 1977

[54] FLOW MEASURING METHOD AND APPARATUS

[75] Inventor: Roderick G. Morrison, Idaho Falls, Idaho

[73] Assignee: TRW Inc., Redondo Beach, Calif.

[22] Filed: Dec. 26, 1973

[21] Appl. No.: 428,270

[52] U.S. Cl. .................................. 73/194 A; 73/53
[51] Int. Cl. ............................................. G01f 1/00
[58] Field of Search ............. 73/194 A, 339 A, 32, 73/32 A, 53, 61 R, 24, 290 V

[56] References Cited

UNITED STATES PATENTS

| | | | |
|---|---|---|---|
| 2,775,748 | 12/1956 | Rod et al. | 73/290 V X |
| 3,115,615 | 12/1963 | Saper | 73/290 V X |
| 3,236,098 | 2/1966 | Dahlke et al. | 73/194 A |
| 3,688,565 | 9/1972 | Brech | 73/67.9 |
| 3,727,454 | 4/1973 | Courty | 73/194 A |
| 3,731,532 | 5/1973 | Courty | 73/194 A |
| 3,738,169 | 6/1973 | Courty | 73/194 A |

FOREIGN PATENTS OR APPLICATIONS 1,079,242  8/1967  United Kingdom ............. 73/290 V Primary Examiner—Charles A. Ruehl
Attorney, Agent, or Firm—Daniel T. Anderson; Donald R. Nyhagen; Jerry A. Dinardo

[57] ABSTRACT

Selected variables of a fluid flowing through a conduit are measured by transmitting acoustic pulses through the conduit wall and fluid stream along normal and oblique transmission paths between acoustic transducers located externally of the conduit, measuring the transit times of the pulses between the transducers, and combining these transit times with certain conduit and transducer parameters according to predetermined mathematical relationships to obtain the values of the variables. The variables which may be measured are flow velocity, mass flow rate, sonic velocity of the fluid, fluid compressibility, fluid temperature, and fluid density.

10 Claims, 3 Drawing Figures

FLOW MEASURING METHOD AND APPARATUS

BACKGROUND OF THE INVENTION

1. Field of the Invention

This invention relates generally to the field of fluid flow measurement and more particularly to a novel acoustic method and instrument for measuring the mass flow rate and certain other related variables of a fluid flowing through a conduit.

2. Prior Art

There are numerous methods of measuring fluid flow. These measurements are generally inferred from the pressure drop measurement across an obstruction placed in a flow path. Examples are venturi meters, orifice meters, nozzle meters, pitot tube meters, or devices which use suction effects to measure a pressure differential. These "head" type meters all have one common disadvantage, that being flow obstruction. Accordingly, the flow measurement obtained is not average flow, but modified flow, thus requiring a correction factor to obtain a relative indication of flow. Another distinct disadvantage of these devices is that they lose accuracy as the diameter of the flow line and velocity of flow increase.

Mass flow is usually measured by positive displacement meters. In these meters, a movable area of known dimension is mounted in the flow line in such a way that the action of the fluid on the area produces a torque or other positive form of measurable pressure. Included in this class of meters are turbine, piston, and cam meters. The common disadvantage of such positive displacement meters is, again, flow obstruction and loss of accuracy as the conduit size increases. Also, none of the devices measure average flow, but rather flow in a confined area which must then be correlated to an average flow.

Ultrasonic flow measurement techniques have also been devised. An article entitled "Electronic Flowmeter System", in the Review of Scientific Instruments, March 1954, Vol. 25, page 201, for example describes an ultrasonic flow measurement system involving the technique of electronically switching from one transducer to another attached to the outside of a conduit. This system measures the phase relationship between upstream and downstream signal transmissions which can be correlated to obtain a measurement of the fluid velocity. If a sufficiently high carrier frequency is employed, this system has the ability to measure flow accurately in conduits as small as one-quarter inch in diameter. The sensitivity of the receiving crystal is a limiting factor, however, which makes the shielding requirements of the electronic circuitry too severe for wide spread use of the system.

Another article entitled "Ultrasonic Flowmeter", in Instruments and Automations, Vol. 28, page 1912, November 1955, describes an ultrasonic flowmeter system which employs two transmitters and two receivers attached to the inside of the conduit. This system requires pipe penetration and measures phase relationship of the transmitted and received ultrasonic signals.

A system which utilizes the flow measuring techniques outlined above in conjunction with a density measuring system including a transducer mounted on the conduit wall to obtain mass flow rate is described in "Process Instruments and Control Handbook", at page 4-89, McGraw-Hill Publishers, 1957. By taking the output of the two systems, mass flow rate is computed electronically. This device requires pipe penetration which is a disadvantage.

Several other ultrasonic flow measurement systems which use the principle of dual path or single path transmission of ultrasonic signals within the conduit have been described in the literature as follows:

Forgacs, R. L., "Precision Ultrasonic Velocity Measurements", Electronics, page 98, Nov. 18, 1960

Messias, H. F., "Ultrasonic Measure Flow Velocity of River", Electronics, page 56, Oct. 13, 1961

Brown, A. E., "Dual Path Ultrasonic Flow Measurements of Fluid Flow", Review of Scientific Instruments, page 1181, September, 1966

Brown, A. E., "Ultrasonic Flow Measurement", Instrument and Control Systems, page 130, March 1967.

Ultrasonic flow measurement systems are also found in the prior patent art. Flow measurement systems of this class, for example, are described in the following patents:

| | |
|---|---|
| 3,336,801 | 3,443,433 |
| 3,349,614 | 3,470,734 |
| 3,402,606 | 3,486,381 |
| 3,420,102 | 3,546,935 |
| 3,426,593 | 3,555,880 |

SUMMARY OF THE INVENTION

This invention provides an improved acoustic method and instrument for measuring certain variables of a fluid flowing through a conduit. These variables are flow velocity, mass flow rate, sonic velocity (i.e. velocity of sound in the fluid), compressibility, temperature, and density.

According to one aspect of the invention, the fluid variables are measured by transmitting acoustic pulses through the conduit wall and fluid stream along transmission paths normal to and oblique to the conduit axis between acoustic transducers located externally of the conduit, measuring the transit times of the pulses along the two paths, and combining these transit times with certain conduit and transducer parameters according to predetermined mathematical relationships to obtain the values of the variables. One unique feature of the invention in this regard resides in the fact that the transit times of the acoustic pulses along the oblique transmission path are measured in both directions of pulse transmission along the path to cancel out the effect of temperature on the flow measurement.

Another aspect of the invention is concerned with a novel acoustic transducer design for use in the present flow metering invention. This design permits the transducers to be located externally of the fluid conduit. This external location eliminates the need to penetrate the conduit wall, avoids obstruction of the flow passages and permits rapid repair and replacement of the transducers. The transducer is uniquely designed to couple maximum acoustic energy into the fluid stream and locate the transducer crystals away from the conduit wall. This remote location of the crystals from the wall effectively isolates the crystals from any hostile environment, i.e. temperature, radiation, etc., which may exist in the vicinity of the wall.

DESCRIPTION OF THE PREFERRED EMBODIMENTS

Figure 1:
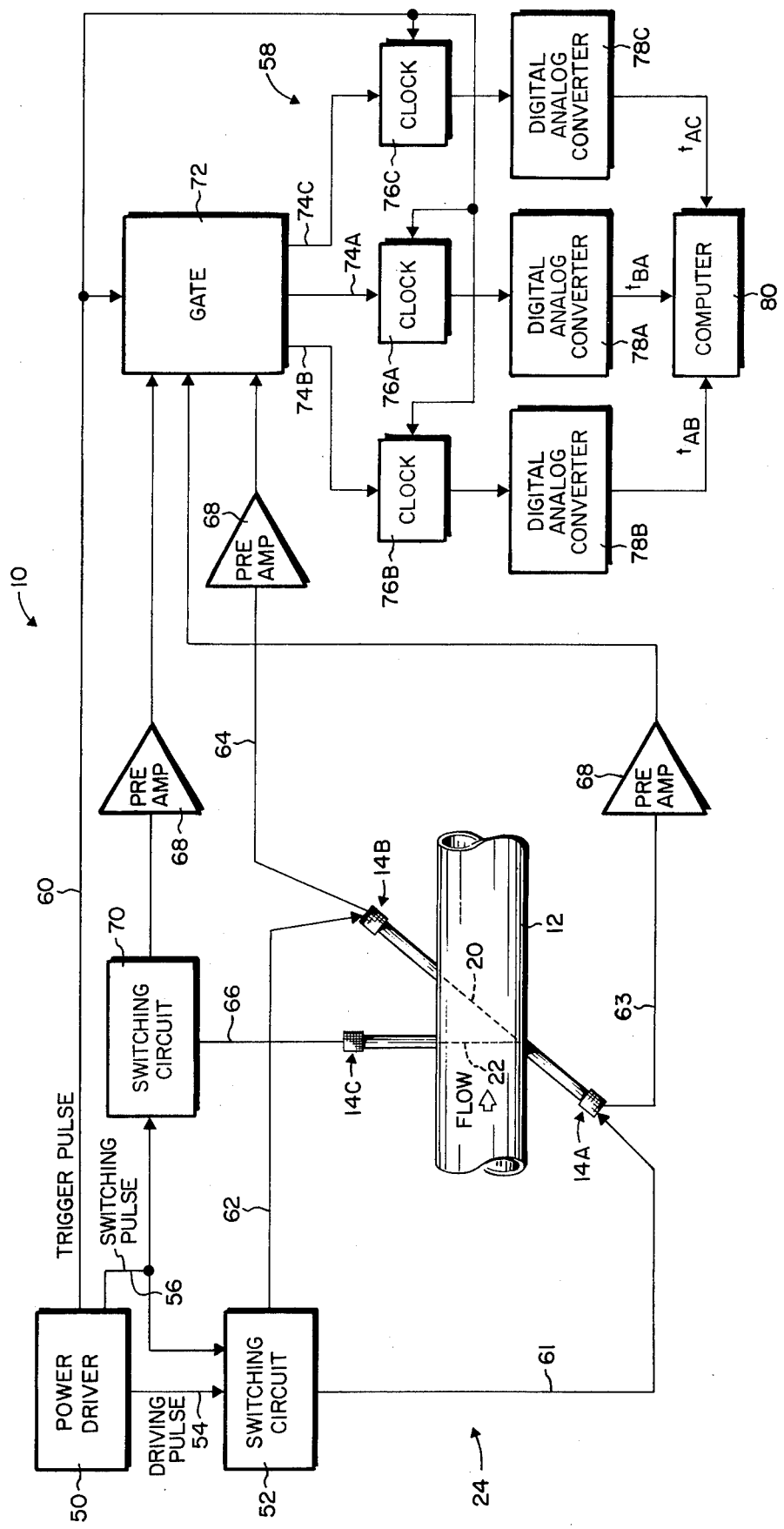
FIG. 1 is a circuit diagram of a flow measuring instrument according to the invention.

The flow measuring instrument 10 illustrated in FIG. 1 provides readouts representing selected variables of a fluid flowing through a conduit 12. These variables may include one or more of the following variables: flow velocity, sonic velocity through the fluid, mass flow rate, fluid compressibility, fluid temperature, fluid density. Flow measuring instrument 10 has three acoustic transducers 14A, 14B, and 14C acoustically coupled to the outside of the conduit 12. These transducers will be described in detail later. Suffice it to say at this point that each transducer includes a transducing crystal 16 (FIG. 3) mounted in a body 18 which transmits and receives acoustic waves between the crystal and the conduit wall.

Transducer 14A is located at one side of the conduit 12 and transducers 14B, 14C are located at the opposite side of the conduit. Transducers 14A, 14B are aligned on a common axis 20 inclined at an oblique angle $\theta$ (FIG. 2) relative to the longitudinal axis of the conduit in such a way that transducer 14B is located downstream of transducer 14A with respect to the direction of fluid flow through the conduit. Transducer 14C is located diametrically opposite transducer 14A on an axis 22 normal to the conduit axis and intersecting the axis 20 at the inner conduit wall surface.

Connected to the transducers 14A, 14B, and 14C is a transducer driving and output monitoring circuit 24. This circuit, like the transducers, will be described in detail later. Suffice it to say here that the circuit periodically excites the transducers 14A, 14B alternately with short duration voltage pulses to effect transmission of short duration ultrasonic acoustic pulses from transducer 14A to transducers 14B and 14C and from transducer 14B to transducer 14A in alternate fashion. Acoustic pulses travel between transducers 14A and 14B through the conduit wall as well as through the fluid within the conduit along a path coinciding with the oblique transducer axis 20. This path is referred to herein as an oblique transmission path. Acoustic pulses travel between transducer 14A, 14C through the conduit wall, as well as through the fluid along a path which coincides with the normal transducer axis 22. This latter path is referred to as a normal transmission path.

Circuit 24 also measures the transit times of the acoustic pulses between the transducers 14A, 14B, and 14C along the oblique and normal transmission paths 20, 22 and converts these transit times to readouts representing one or more of the fluid variables listed earlier, i.e. flow velocity, mass flow rate, sonic velocity through the fluid, fluid compressibility, fluid temperature, and fluid density.

Figure 2:
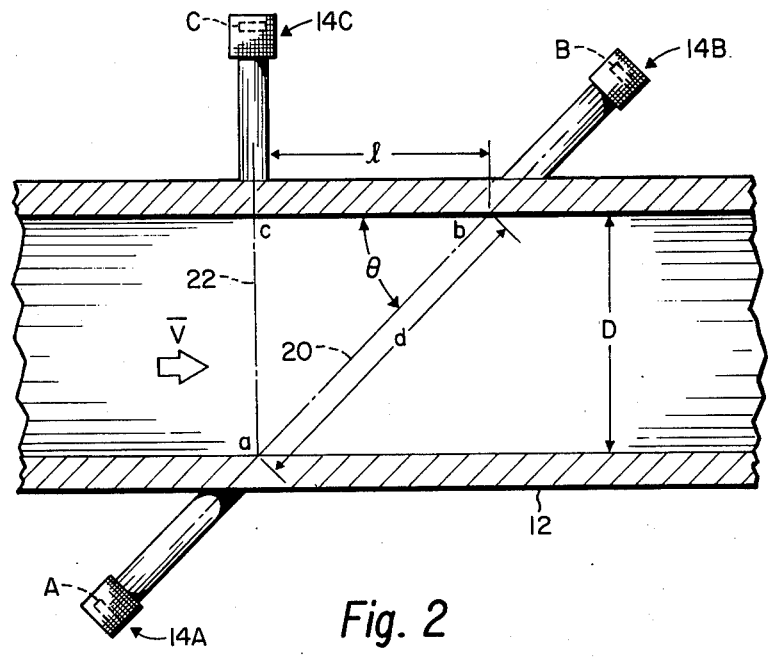
FIG. 2 is an enlarged section through the flow conduit showing the acoustic transducers of the instrument.

Before proceeding with a more detailed description of the flow measuring instrument 10, it is well to consider the relationships between the measured transit times and the listed fluid variables. In this regard, attention is directed to FIG. 2, illustrating the geometrical relationship of the transducers 14A, 14B and 14C, and the conduit 12. In this figure, $a$, $b$, and $c$ denote the intersection points of the transducer axes 20, 22 with the inner conduit wall. The reference characters $d$, $l$, $D$, denote, respectively, the length ($d$) of the oblique acoustic transmission path 20 between points $a$ and $b$, the distance ($l$) along the conduit between points $b$ and $c$, and the inner conduit diameter ($D$) (and hence the length of the normal acoustic transmission path 22 between points $a$ and $c$). The crystals 16 of the transducers 14A, 14B, and 14C are designated as A, B, and C in FIG. 2.

It is significant to note here that the transducers 14A, 14B, and 14C are essentially identical, such that the transit times of the acoustic pulses between their crystals and their respective adjacent axis intersection points $a$, $b$, and $c$ are equal.

The relationships between the measured transit times of the acoustic pulses between the transducers and the fluid variables listed above will not be derived. The following quantities are used in this derivation:

$\overline{V}$ = average flow velocity (ft/sec)

$\overline{C}$ = average sonic velocity of the fluid (ft/sec)

$\dot{m}$ = average mass flow rate (lb$_m$/sec)

$\overline{K}$ = average compressibility of liquid (ft$^2$/lb$_f$)

$\overline{T}$ = average fluid temperature (° F)

$\overline{\rho}$ = average fluid density (lb$_m$/ft$^3$)

$t_{AB}$ = sonic transit time from crystal A to crystal B $t_{BA}$ = sonic transit time from crystal B to crystal C $t_{AC}$ = sonic transit time from crystal A to crystal C $t_{ab}$ = sonic transit time through the fluid from $a$ to $b$ $t_{ba}$ = sonic transit time through the fluid from $b$ to $a$ $t_{ac}$ = sonic transit time through the fluid from $a$ to $c$ $\Delta t$ = difference in transit time from crystal B to crystal A $t_1$ = sonic transit time between crystal A and point $a$ $t_2$ = sonic transit time between crystal B and point $b$ $t_3$ = sonic transit time between crystal C and point $c$ The average flow velocity $\overline{V}$ is obtained in terms of the measurable and known quantities by employing the geometric relationships illustrated in FIG. 2. The effective downstream fluid sound velocity along the oblique path = $C + \overline{V} \cos \theta$, and the effective upstream fluid sound velocity along this path = $C - \overline{V} \cos \theta$, therefore $$t_{AB} = \frac{d}{C + \overline{V} \cos \theta} + t_1 + t_2 \qquad (1)$$

and $$t_{BA} = \frac{d}{C - \overline{V} \cos \theta} + t_1 + t_2 \qquad (2)$$

The difference in upstream and downstream sonic transit times is thus $$t = t_{BA} - t_{AB} = d \left( \frac{1}{C - \overline{V} \cos \theta} - \frac{1}{C + \overline{V} \cos \theta} \right) \qquad (3)$$

For $V \ll C$, the average fluid flow velocity can be obtained from equation (3) as $$\overline{V} \cong \frac{t\, C^2}{2d \cos \Theta} = \frac{(t_{BA} - t_{AB})\, C^2}{2l} \quad (4)$$

or is in the exact form $$\overline{V} = \frac{1}{\cos \Theta} \left( \sqrt{\frac{d^2}{\Delta t^2} + C^2} - \frac{d}{\Delta t} \right) \quad (5)$$

From FIG. 2, C is given by $$C = \frac{d}{t} = \frac{D}{t_{ac}} \quad (6)$$

where $$\overline{t} = \frac{t_{ab} + t_{ba}}{2} \text{ (through the fluid only)}$$

and $t_{ac}$ = sonic transit time from point $a$ to $c$ through the fluid only. Thus, by substituting equation (6) into equation (4), we obtain $$\overline{V} \cong \frac{(t_{BA} - t_{AB})\, D^2}{2l\, (t_{ac})^2} \quad (7)$$

To obtain $\overline{V}$, We must be able to calculate $t_{ac}$ from $t_{AB}$, $t_{BA}$, and $t_{AC}$. Solving for $t_{ac}$ from equation (6)

$$t_{ac} = \frac{D}{d}\, \overline{t} \quad (8)$$

The average of the upstream and downstream sonic transit times is given by $$\frac{t_{AB} + t_{BA}}{2} = \frac{t_1 + t_2 + t_{ab} + t_2 + t_1 + t_{ba}}{2}$$

but since $t_1 = t_2 = t_3$, $$\frac{t_{AB} + t_{BA}}{2} = 2t_1 + \overline{t} \quad (9)$$

The cross flow sonic transit time $t_{AC}$ is given by $$t_{AC} = t_1 + t_3 + t_{ac} = 2t_1 + t_{ac}$$

and $$2t_1 = t_{AC} - t_{ac} \quad (10)$$

Substituting equation (10) into equation (9)

$$\frac{t_{AB} + t_{BA}}{2} = t_{AC} - t_{ac} + \overline{t}$$

and $$\overline{t} = \frac{t_{AB} + t_{BA}}{2} + t_{ac} - t_{AC} \quad (11)$$

Substituting equation (11) into equation (8), $t_{ac}$ can be obtained in terms of measurable quantities $$t_{ac} = \frac{D}{d} \left[ \frac{t_{AB} + t_{BA}}{2} + t_{ac} - t_{AC} \right]$$

Solving for $t_{ac}$, one obtains $$t_{ac} = \frac{D}{d - D} \left[ \frac{t_{AB} + t_{BA}}{2} - t_{AC} \right] \quad (12)$$

Now substituting equation (12) into equation (7), V is obtained in terms of measurable quantities $$\overline{V} = \frac{(t_{BA} - t_{AB})\, D^2}{2L\, \dfrac{D^2}{(d-D)^2} \left( \dfrac{t_{AB} + t_{BA}}{2} - t_{AC} \right)^2}$$

Simplifying, the above equation becomes $$\overline{V} = \frac{(t_{BA} - t_{AB}) \left( \sqrt{D^2 + l^2} - D \right)^2}{2l \left( \dfrac{t_{AB} + t_{BA}}{2} - t_{AC} \right)^2} \quad (13)$$

Substituting equation (12) into equation (6) the sonic velocity, C is obtained in terms of measurable quantities.

$$C = \frac{D}{t_{ac}} = \frac{\sqrt{D^2 + l^2} - D}{\dfrac{t_{AB} + t_{BA}}{2} - t_{AC}} \quad (14)$$

Solving for the mass flow rate $\dot{m}$ $$\dot{m} = \overline{\rho}\, \overline{V}\, \frac{\pi D^2}{4} \quad (15)$$

For a liquid, the average density is given by $$\overline{\rho} = \frac{g_c}{KC^2} \quad (16)$$

with K = the compressibility of the liquid $$g_c = \text{gravitational constant } \frac{32.2\, lb_m - ft}{lb_f - sec^2}$$

Substituting equations (4) and (16) into (15), $$\dot{m} = \frac{\pi D^2 g_c\, (t_{BA} - t_{AB})\, C^2}{4KC^2\, 2l} = \frac{\pi D^2 g_c\, (t_{BA} - t_{AB})}{8Kl} \quad (17)$$

In order to evaluate K, the average fluid temperature $\overline{T}$ must be known.

Empirical equations relating the temperature, compressibility, and sonic velocity of a given fluid may be obtained from various handbooks. For liquid sodium, for example, the following equations are available from the liquid metals handbook:

$$\overline{T} = 6460 - 0.805C \quad (18)$$

and $$K = [4.70\,\overline{T} + 8157.] \times 10^{-12} \quad (19)$$

Substituting equation (18) into equation (19), K is given by $$K = 3.86 \times 10^{-8} - 3.78 \times 10^{-12}\,C \quad (20)$$

By substituting equation (14) into equation (20) the compressibility is obtained in terms of measurable quantities $$K = (3.86 \times 10^{-8}) - (3.79 \times 10^{-12})\,\frac{\sqrt{D^2 + l^2} - D}{\frac{t_{AB} + t_{BA}}{2} - t_{AC}} \quad (21)$$

The temperature is similarly obtained for substituting equation (14) into equation (18)

$$T(°F) = 6460. - 0.805 \left[\frac{\sqrt{D^2 + l^2} - D}{\frac{t_{AB} + t_{BA}}{2} - t_{AC}}\right] \quad (22)$$

Now the mass flow rate $\dot{m}$ (lb$_m$/sec) can be obtained by substituting equation (21) into equation (17)

$$\dot{m}\left(\frac{\text{lb}_m}{\text{sec}}\right) = \frac{\pi D^2\,(t_{BA} - t_{AB}) \times 10^{12}}{8L\left[1200 - 0.2356\left(\frac{\sqrt{D^2 + l^2} - D}{t_{AB} + t_{BA} - 2t_{AC}}\right)\right]} \quad (23)$$

Now $\overline{\rho}$ can be obtained from equation (16) by substituting in equations (14) and (20)

$$\overline{\rho} = \frac{g_c}{KC^2} = \frac{g_c \times 10^{12}}{386C^2 - 3.79C^3}$$

or $$\overline{\rho}\left(\frac{\text{lb}_m}{\text{ft}^3}\right) = \frac{1 \times 10^{12}}{1200.\left(\frac{\sqrt{D^2 + l^2} - D}{\frac{t_{AB} + t_{BA}}{2} - t_{AC}}\right)^2 - 0.1178\left(\frac{\sqrt{D^2 + l^2} - D}{\frac{t_{AB} + t_{BA}}{2} - t_{AC}}\right)^3} \quad (24)$$

Thus, all the earlier listed fluid variables can be obtained from measured and known times and physical constants, as follows:

$\overline{V}$ (ft/sec) from equation (13)

$C$ (ft/sec) from equation (14)

$\dot{m}$ (lb$_m$/sec) from equation (23)

$K$ (ft$^2$/lb$_f$) from equation (21)

$T$ (°F) from equation (22)

$\overline{\rho}$ (lb$_m$/ft$^3$) from equation (24)

} for liquid sodium

The mass flow rate $\dot{m}$, compressibility K, temperature T, and density $\overline{\rho}$ for fluids other than liquid sodium can also be obtained, of course, using appropriate handbook data similar to that used above for liquid sodium.

Continuing now with the description of the flow measuring instrument 10, the transducers 14A, 14B, and 14C are essentially identical and, accordingly, a description of one will suffice for all. Transducer 14C will be described by reference to FIG. 3. The transducer includes an acoustic transmission member or rod 26 in the form of a metal tube or pipe. One end face 27 of this rod is firmly joined, as by brazing or welding, to the outer surface of the conduit 12. This end of the rod is curved to seat against the conduit with the end surface of the rod in face-to-face contact with the outer surface of the conduit. Mounted on the other end of the transmission rod is an acoustic transducer assembly 28.

Figure 3:
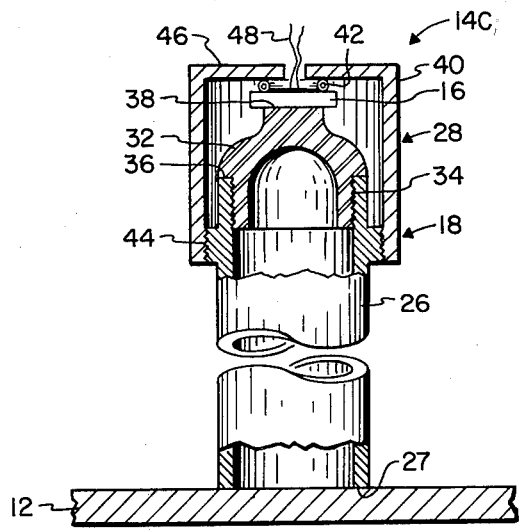
FIG. 3 is an enlarged section through a transducer.

Transducer assembly 28 comprises a piezo-electric crystal 16 coupled to the transmission rod 26 by a crystal holder or support 32. This crystal support has an inverted or bowl-like (bullhorn) shape and is joined to the outer end of the transmission rod by mating internal and external threads 34 on the rod and support, respectively. The crystal support has an annular axially presented shoulder surface which seats flat against the end face of the rod to provide an interface 36 between the support and rod. The upper end of the support, as viewed in FIG. 3, is reduced in diameter and terminates in a flat end face 38 which seats the crystal 16. Crystal 16 is held in position on the support 32, in firm contact with the support face 38, by a compression cap or cover 40 and a compression ring 42. Compression cover 40 is threaded on the transmission rod 26 at 44 and has an end wall 46 which seats against the compression ring 42 to press the latter firmly against the crystal 16. This compression ring is a resilient ring, such as an O-ring, and holds the crystal firmly against the crystal support face 38. Cover wall 46 has an opening through which the crystal leads 48 extend for connection to the circuit 24 in the manner explained presently.

Transducers 14A and 14B are identical to the transducer 14C, just described, except for the angles of their concave conduit seating faces 27. Thus, the seating face 27 of transducer 14C is generally perpendicular to the longitudinal axis of the transducer, that is tangent to a plane perpendicular to the transducer axis, such that when the transducer is placed on the conduit 12, the transducer axis is positioned normal to the conduit axis. The concave conduit seating faces of transducers 14A, 14B, on the other hand, are inclined at the angle $\theta$ relative to the transducer axes, that is the seating faces are tangent to a plane inclined at the angle $\theta$ to the transducer axes, such that when these transducers are placed on the conduit, their axes are positioned at the angle $\theta$ relative to the conduit axis. As noted earlier, the transducers are designed so that the sonic transit times $t_1$, $t_2$, and $t_3$ between their crystals 16 and respective axis intersection points $a$, $b$, and $c$ are equal.

From the description to this point, it will be understood that when transducer 14A is energized by application of an ultrasonic electrical driving pulse to its crystal 16, an ultrasonic acoustic pulse is transmitted through the transducer crystal support 32 and transmission rod 26 to the wall of conduit 12. A portion of this acoustic pulse energy is transmitted through the conduit wall to the transducers 14B, 14C and another portion of the pulse energy is transmitted through the fluid in the conduit to the latter transducers along the acoustic paths 20, 22. Similarly, when transducer 14B is energized, the resulting ultrasonic acoustic pulse in transmitted to transducer 14A partly through the conduit wall and partly through the fluid along acoustic path 22. As will be explained presently, the instrument circuit 24 measures the pulse transit times $t_{AB}$, $t_{AC}$, and $t_{BA}$ through the fluid only and converts these transit times to the fluid variables mentioned earlier.

Transducers 14A, 14B, and 14C are arranged to couple acoustic energy from their crystals 16 into the fluid within the conduit 12 in such a way that the acoustic energy emerges from the inner conduit wall surface into the fluid at a zero node of the acoustic frequency to accomplish maximum acoustic energy transmission from the crystal into the fluid. To this end, the crystal holder or support 32 of each transducer is shaped and constructed of an appropriate material to provide an impedance match between its transducer crystal 16 and transmission rod 26. The transducer dimensions between the crystal and interface 36 and between the interface and conduit seating face 27 are made such, relative to the conduit wall thickness, as to provide a tuned acoustic circuit wherein acoustic waves propagating from the crystal to the conduit wall traverse the interface 36 at a zero node and then emerge from the inner conduit wall surface into the fluid within the conduit at a zero node of the characteristic acoustic frequency.

Turning now to FIG. 1, the flow meter circuit 24 comprises a transducer drive 50 for generating periodic voltage pulses each of ultrasonic frequency and very short duration for exciting the crystals 16 of the transducers 14A, 14B to generate the acoustic pulses which are transmitted through the wall of and the fluid within the conduit 12, as explained earlier and discussed in more detail presently.

These voltage pulses may have an ultrasonic frequency on the order of 2 Mhz and a rise time on the order of 50 nanoseconds. In addition to the transducer driving pulses, the transducer drive 50 generates timing or trigger pulses which commence concurrently with the driving pulses and switching signals synchronized with the pulses.

The transducer driving pulses and switching signals from the transducer driver 50 are fed to a switching circuit 52 through signal leads 54, 56, respectively. The trigger pulses from the driver are fed to a transducer output receiver 58 through a signal lead 60.

Switching circuit 52 has two different switching states. In one switching state, the switching circuit feeds the incoming transducer driving pulses from the transducer driver 50 through a signal lead 61 to the transducer 14A. In its other switching state, the switching circuit feeds the incoming driving pulses to the transducer 14B through a signal lead 62. The switching signals from the driver shift to the switching circuit between its switching states in timed relation to the incoming driving pulses to the switching circuit in a manner such that the successive driving pulses are fed to the transducers 14A, 14B in alternate fashion. From this description, it will be understood that the crystals 16 of the transducers 14A, 14B are excited alternately.

As noted earlier, each transducer 14A, 14B, when excited by a driving pulse from the transducer driver 50, produces an ultrasonic acoustic pulse which propagates from the transducer crystal 16, through the transducer body to the wall of conduit 12, then through both the conduit wall and the fluid within the conduit to the opposing transducer or transducers, and finally through the body of each latter transducer to its crystal. The propagation velocity of the acoustic pulses through the conduit wall is substantially greater than the propagation velocity through the fluid. As a consequence, the crystal of each receiving transducer receives two successive acoustic pulses for each acoustic pulse generated by the excited transmitting transducer. The first pulse received is that which propagates through the conduit wall. The second pulse received is that which propagates through the fluid in the conduit. The crystal of each receiving transducer generates an electrical output pulse in response to each arriving acoustic pulse.

When the transducer 14A is excited or driven by a driving pulse from the driver oscillator 50, the transducers 14B, 14C receive the resulting acoustic pulses through the conduit wall and through the fluid along the oblique and normal acoustic transmission paths 20, 22, respectively. When the transducer 14B is driven, transducer 14A receives the resulting acoustic pulses along through the conduit wall and through the fluid along the oblique path 20. Transducer 14C, of course, also receives acoustic pulses from the transducer 14B and produces corresponding electrical output pulses. As explained below, these latter output pulses from transducer 14C are not utilized.

Returning to FIG. 1, the output pulses from transducers 14A, 14B, and 14C are fed to the receiver 58 through connections 63, 64, and 66 each including an amplifier 68. The connection 66 between transducer 14C and the receiver 58 also includes a switching or gating circuit 70 controlled by the switching signals from the transducer driver 50. Gating circuit 70 has two states, a blocking state in which the circuit blocks passage of output pulses from the transducer 14C and a conducting state in which the circuit passes the output pulses from the transducer 14C. The gating circuit 70 is controlled by the switching signals from the driver 50 in a manner such that the circuit is placed in its conducting state each time the transducer 14A is excited by a driving pulse from the driver and in its blocking state each time the transducer 14B is excited by a driving pulse.

From the description to this point, it will be understood that each time the transducer 14A is excited by a driving pulse from the transducer driver 50, the receiver 58 receives an initial amplified output pulse and a following amplified output pulse from each of the transducers 14B, 14C. Each time the transducer 14B is excited by the driver, the receiver receives an initial amplified output pulse and a following amplified output pulse from the transducer 14A. In each case, the initial output pulse from each receiving transducer is generated by the acoustic pulse which propagates from the excited transducer to the receiving transducer through the wall of conduit 12 and is hereafter referred to as a false output pulse. The following output pulse from each receiving transducer is generated by the acoustic pulse which propagates from the excited transducer to the receiving transducer through the fluid in the conduit and is hereafter referred to as a true output pulse, or simply a true pulse. The time lag between the true and false pulses is the difference in the propagation time of the acoustic pulses through the conduit wall and the fluid. The time duration of the driving pulses and resulting acoustic pulses is made small in comparison to this lag time.

It will be recalled that each time the driver 50 generates a driving pulse for exciting transducer 14A or 14B, the driver also generates a timing or trigger pulse. This trigger pulse commences simultaneously with the driving pulse, and is fed directly to the receiver 58 through the signal lead 60. Accordingly, the trigger pulse arrives at the receiver prior to the transducer output pulses produced by the driving pulse. Thus, during each pulse generating cycle of the driver 50, the receiver 58 receives, in the order listed, an initial trigger pulse from the driver, a following false output pulse from each receiving transducer, and a final true output pulse from each receiving transducer.

Receiver 58 includes an input gating circuit 72 which receives the output pulses from the transducers 14A, 14B, and 14C and is controlled by the trigger pulses from the driver 50 in a manner such that the circuit blocks the false transducer output pulses and passes only the true transducer output pulses. To this end, the gating circuit has a blocking state and a conducting state. In its blocking state, the circuit blocks the incoming transducer output pulses. In its conducting state, the circuit passes or transmits the incoming transducer output pulses. Each trigger pulse received by the gating circuit momentarily triggers the circuit to its blocking state for a period of time sufficient to block the initial false transducer output pulse or pulses which as just noted, arrive at the receiver immediately following each trigger pulse. The gating circuit then assumes its conducting state in time to pass or transmit the following true output pulse or output pulses from the transducers.

It will now be understood that each time the transducer 14A is excited by a driving pulse from the transducer driver 50, the gating circuit 72 receives false and true output pulses from the transducers 14B, 14C and passes only the true pulses. These true pulses appear at outputs 74B, 74C, respectively, of the gating circuit. Each time the transducer 14B is excited by a driving pulse, the gating circuit receives false and true output pulses from the transducer 14A and passes only the true pulse. This true output pulse appears at output 74A of the gating circuit.

The gating circuit outputs 74A, 74B, and 74C are connected to timing or clock circuits 76A, 76B, and 76C, respectively. These clock circuits also receive the trigger pulses from the driver 50 through signal lead 60. Each time the transducer 14A is exited by a driving pulse from the driver 50, clock circuits 76B, 76C receive initial trigger pulses from the driver and following true output pulses from the transducers 14B, 14C through the gating circuit 72. Each time the transducer 14B is excited by a driving pulse, clock circuit 76A receives an initial trigger pulse from the driver 50 and a following true output pulse from the transducer 14A through the gating circuit. Each clock circuit measures and produces a digital output representing the elapsed time between each incoming trigger pulse and following true transducer output pulse. The elapsed times measured by the clock circuits will be recognized to be the transit times $t_{AB}$, $t_{AC}$, and $t_{BA}$ referred to earlier, that is the transit times of the acoustic pulses from the crystal 16 of the excited transducer through the fluid in the conduit 12 along one of the acoustic transmission paths 20, 22 to the crystal or crystals of the receiving transducer or transducers.

Thus, each time transducer 14A is excited by a driving pulse from the driver 50, clock circuit 76B produces a digital output representing the transit time $t_{AB}$ of the corresponding acoustic pulse from the crystal 16 of transducer 14A, through the fluid in conduit 12 along the oblique acoustic transmission path 20, to the crystal of transducer 14B. Clock circuit 76C simultaneously produces a digital output representing the transit time $t_{AC}$ of the acoustic pulse from the crystal of transducer 14A, through the fluid along the normal acoustic transmission path 22, to the crystal of transducer 14C. Similarly, each time transducer 14B is excited by a driving pulse, clock circuit 76A produces a digital output representing the transit time $t_{BA}$ of the corresponding acoustic pulse from the crystal of transducer 14B, through the fluid along the oblique acoustic path 20, to the crystal of transducer 14A.

The digital transit time outputs of the clock circuits 76A, 76B, and 76C are fed to digital-to-analog converters 76A, 76B, and 76C, respectively, which convert the digital time inputs to corresponding analog time outputs. The outputs of these converters are data which may be fed to a computer 80 with appropriate computer circuitry for combining the analog time inputs in accordance with any one or more of the earlier mentioned flow equations (13), (14), (21), (22), (23), or (24), to yield the corresponding flow quantity or flow quantities, as follows:

| | |
|---|---|
| average flow velocity ($\bar{V}$) | equation (13) |
| average sonic velocity of fluid ($c$) | equation (14) |
| average fluid compressibility ($K$) | equation (21) |

| -continued | |
|---|---|
| average fluid temperature ($T$) | equation (22) |
| average mass flow rate ($\bar{m}$) | equation (23) |
| average fluid density ($\bar{\rho}$) | equation (24) |

I claim:

1. The method of measuring selected variables of a fluid flowing through a conduit comprising the steps of:
   transmitting first acoustic pulses through said fluid between first pulse transmitting and receiving positions located at opposite sides of the conduit passage and along a first path crossing said passage normal to and intersecting the conduit axis in a manner such that the pulse transit times between said positions and the adjacent points of intersection of said path with the passage wall are in a known ratio;
   transmitting second acoustic pulses through said fluid between second pulse transmitting and receiving positions located at opposite sides of the conduit passage and along a second path crossing said passage at an oblique angle to and intersecting the conduit axis in a manner such that the pulse transit times between said second positions and the adjacent points of intersection of said second path with said passage wall are in a known ratio;
   one of said first positions and one of said second positions coinciding and the path intersection points adjacent said coincident positions also coinciding;
   measuring and producing an electrical output representing the transit time of said first pulses between said first positions;
   measuring and producing an electrical output representing the transit time of said second pulses between said second positions; and
   said outputs being adapted to be combined in accordance with selected mathematical equations to obtain any of the following fluid variables: flow velocity, sonic velocity, compressibility, temperature, mass flow rate, or density.

2. The method according to claim 1 wherein said ratios equal unity.

3. The method according to claim 1 wherein: pulses are transmitted in each direction along said oblique path.

4. The method according to claim 1 wherein: each of said measuring steps comprises generating a timing pulse concurrently with each acoustic pulse, generating an electrical signal pulse in response to arrival of each acoustic pulse at said pulse receiving positions, and measuring the elapsed time between each timing pulse and each corresponding signal pulse.

5. The method according to claim 1 including the additional step of:
   combining said electrical outputs in accordance with at least one of said equations to obtain the corresponding fluid variable.

6. Apparatus for measuring selected variables of a fluid flowing through a conduit, comprising
   means for transmitting first acoustic pulses through said fluid between first pulse transmitting and receiving positions located at opposite sides of the conduit passage and along a first path crossing said passage normal to and intersecting the conduit axis in a manner such that the pulse transit times between said positions and the adjacent points of intersection of said path with the passage wall are in a known ratio;
   means for transmitting second acoustic pulses through said fluid between second pulse transmitting and receiving positions located at opposite sides of the conduit passage and along a second path crossing said passage at an oblique angle to and intersecting the conduit axis in a manner such that the pulse transit times between said second positions and the adjacent points of intersection of said second path with said passage wall are in a known ratio;
   one of said first positions and one of said second positions coinciding and the path intersection points adjacent said coincident positions also coinciding;
   means for measuring and producing an electrical output representing the transit time of said first pulses between said first positions;
   means for measuring and producing an electrical output representing the transit time of said second pulses between said second positions; and
   said outputs being adapted to be combined in accordance with selected mathematical equations to obtain any of the following fluid variables: flow velocity, sonic velocity, compressibility, temperature, mass flow rate, or density.

7. Apparatus according to claim 6 wherein:
   said ratios equal unity.

8. Apparatus according to claim 6 wherein:
   said second pulse transmitting means comprises means for transmitting pulses in each direction along said oblique path.

9. Apparatus according to claim 6 wherein:
   each of said measuring means comprises means for generating a timing pulse concurrently with each acoustic pulse, means for generating an electrical signal pulse in response to arrival of each acoustic pulse at said pulse receiving positions, and means for measuring the elapsed time between each timing pulse and each corresponding signal pulse.

10. Apparatus according to claim 6 including:
    means for combining said electrical outputs in accordance with at least one of said equations to obtain the corresponding fluid variable.

* * * * *